(12) United States Patent
Horne et al.

(10) Patent No.: US 9,615,914 B2
(45) Date of Patent: Apr. 11, 2017

(54) APPARATUS AND METHODS FOR NIPPLE AND BREAST FORMATION

(75) Inventors: Kenneth N. Horne, San Francisco, CA (US); Michael H. Rosenthal, Menlo Park, CA (US); Geoffrey C. Gurtner, Stanford, CA (US); Christopher S. Jones, Menlo Park, CA (US); Sergio Salinas, Redwood City, CA (US); Joseph Rimsa, Palo Alto, CA (US)

(73) Assignee: TauTona Group Research and Development Company, L.L.C., Redwood City, CA (US)

( * ) Notice: Subject to any disclaimer, the term of this patent is extended or adjusted under 35 U.S.C. 154(b) by 325 days.

(21) Appl. No.: 13/277,464

(22) Filed: Oct. 20, 2011

(65) Prior Publication Data

US 2012/0101575 A1    Apr. 26, 2012

Related U.S. Application Data

(60) Provisional application No. 61/405,120, filed on Oct. 20, 2010.

(51) Int. Cl.
| A61F 2/12 | (2006.01) |
| A61F 2/52 | (2006.01) |
| A61J 13/00 | (2006.01) |

(52) U.S. Cl.
CPC .......... *A61F 2/12* (2013.01); *A61F 2002/526* (2013.01); *A61J 13/00* (2013.01)

(58) Field of Classification Search
CPC .................. A61F 5/03; A61F 2002/526; A61F 2250/0018

USPC ... 623/7, 8, 11.11, 15.12, 23.72, 23.76, 901, 623/909; 600/37, 38; 128/890
See application file for complete search history.

(56) References Cited

U.S. PATENT DOCUMENTS

| 1,922,947 | A | | 8/1933 | Grotte |
| 4,778,465 | A | | 10/1988 | Wilkins |
| 4,790,309 | A | | 12/1988 | Becker |
| 5,824,076 | A | * | 10/1998 | Knowlton ......................... 623/8 |
| 2008/0071370 | A1 | * | 3/2008 | Vinas ................................ 623/7 |
| 2010/0312354 | A1 | * | 12/2010 | Bandoh ..................... A61F 2/36 623/23.15 |

FOREIGN PATENT DOCUMENTS

| JP | 11-514892 | 12/1999 |
| WO | WO 97/06756 | 2/1997 |
| WO | WO 2012/054705 | 4/2012 |

* cited by examiner

*Primary Examiner* — Brian Pellegrino
(74) *Attorney, Agent, or Firm* — Levine Bagade Han LLP

(57) ABSTRACT

Apparatus and methods for nipple and breast formation are described where devices precondition or expand a target nipple tissue to reduce the pressure exerted by the skin on an eventual implant. Generally, the apparatus comprises a mold having a contact surface which is curved in conformance with a breast upon which the mold is positionable, the contact surface having an adhesive for securement upon the breast, and the mold defining a cavity along the contact surface which conforms to a size of a nipple to be formed upon the breast and where the cavity further comprises the adhesive for securement to the nipple. A breast enlargement device comprises a cup larger than the target breast and further defines an inner surface which adheres to the breast when contacted.

4 Claims, 16 Drawing Sheets

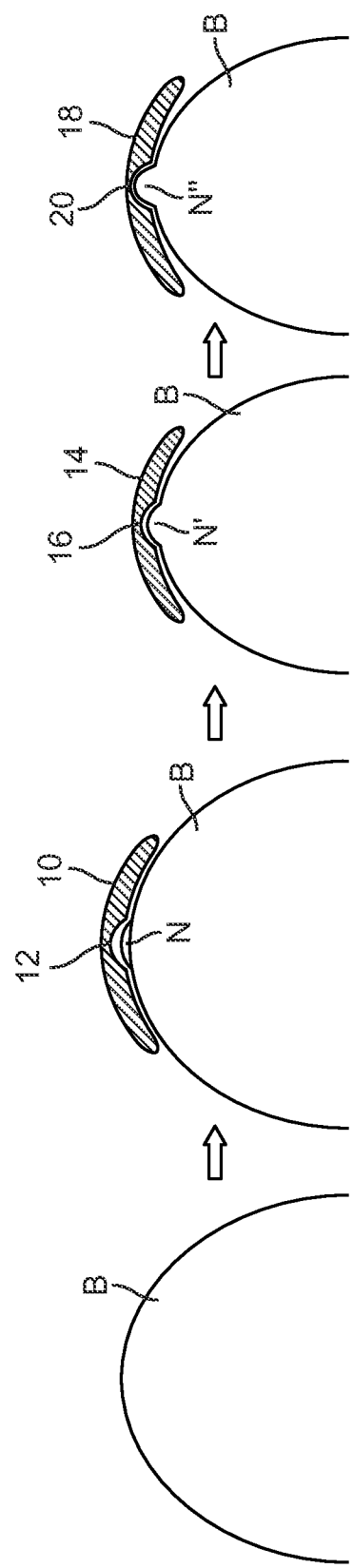

APPARATUS AND METHODS FOR NIPPLE AND BREAST FORMATION

CROSS-REFERENCE TO RELATED APPLICATIONS

This application claims the benefit of priority to U.S. Prov. App. 61/405,120 filed Oct. 20, 2010, which is incorporated herein by reference in its entirety.

FIELD OF THE INVENTION

The present invention relates generally to medical devices and methods used for nipple reconstruction and breast reconstruction and/or enlargement. More particularly, the present invention relates to apparatus and methods for nipple reconstruction and breast reconstruction and/or enlargement utilizing devices which are mechanically simple to utilize.

BACKGROUND OF THE INVENTION

In a majority of mastectomies, the nipple is not preserved. While breast implants are an option for women who would like to have their breasts reconstructed, nipple reconstruction is still a challenging problem which lacks good options. Currently, surgeons do their best to recreate a nipple, e.g., by cutting, folding, and suturing skin together and/or implanting the nipple area with some filler or material such as a biomaterial or some allograft. The inherent challenge is that the skin, which is taut, tends to push any additive material into the body making the nipple appear flat.

Although techniques for nipple-saving mastectomies exist, in most cases, the nipple and areola tissue are removed. There is no established gold standard procedure for nipple reconstruction, however, and with all techniques permanence of nipple projection is inconsistent or problematic, and therein is an unmet clinical need.

An example of a commercially available product that helps enlarge tissue prior to implantation of an expansion material is made by Mentor (Mentor LLC, Santa Barbara, Calif.). For breast reconstruction or augmentation, the balloon-like expander is implanted into the breast in a deflated configuration and then gradually inflated using saline to stretch and condition the breast tissue.

However, such a methodology of using an implantable, expandable balloon is not practical for nipple expansion because of the added surgical complexity in a small tissue volume, and would likely not be adopted by patients who have already gone through months of surgical progressions starting with their mastectomy.

Another example of a commercially available non-surgical, non-implanted product that helps enlarge or precondition breasts prior (for example, prior to fat grafting) is the BRAVA® (Brava, LLC, Miami, Fla.) which is typically worn at night by the user while sleeping.

However, the user is generally required to wear the device for a minimum of 10 hours per day for 10 to 14 consecutive weeks. This is usually very challenging given that a small pump must be worn in addition to the molds and a sports bra-like garment. Patient compliance is often a big challenge with BRAVA®, and further it is not intended for or capable of nipple expansion.

SUMMARY OF THE INVENTION

A nipple forming apparatus which may precondition, expand or maintain a target nipple tissue may be utilized to reduce the pressure exerted by the skin on an implant. Generally, the apparatus may comprise a mold having a contact surface which is curved in conformance with a breast upon which the mold is positionable, the contact surface comprising an adhesive for securement upon the breast, and the mold defining a cavity along the contact surface which conforms to a size of a nipple to be formed or that has been formed by an implant upon the breast and where the cavity further comprises the adhesive for securement to the nipple.

In another variation, the nipple forming apparatus may generally comprise a base having a contact surface for placement upon a surface of a breast and defining an opening sized for positioning of a nipple therethrough, a column extending from the base and defining an opening therethrough, a biasing mechanism positioned at a distal end of the column opposite to the base, wherein the column is threaded such that a height of the biasing mechanism is adjustable relative to the base, and an implant sized to be positioned within the column and which is positionable beneath a surface of the breast in proximity to the base.

In use, a first mold having a contact surface which is curved may be adhered upon a breast such that the mold conforms to a surface of the breast. The mold may further define a first cavity along the contact surface which conforms to a size of a nipple to be formed upon the breast. This mold may be adhered to a portion of the breast where a nipple is to be formed within the cavity and may be maintained upon the breast for a first period of time. The mold may be removed from the breast and at least a second mold having a contact surface may be adhered upon the breast where the second mold defines a second cavity which is larger than the first cavity. The second mold may be maintained upon the breast for a second period of time such that a size of the nipple is maintained when the second mold is removed from the breast.

In yet another variation for nipple formation, an alternative method for forming a nipple may comprise use of the mold subsequent to the formation of a nipple utilizing an implant, e.g., using any of the materials described herein. In this case, an implant may be first implanted within a breast such that a projection is formed approximating the desired shape of the nipple, then a mold having a contact surface which is curved may be adhered upon a breast such that the mold conforms to a surface of the breast. The mold may further define a cavity along the contact surface which conforms to a size of the nipple formed upon the breast and the nipple may be further adhered to the inner surface of the cavity via an adhesive. The mold may then be maintained upon the breast for a period of time such that a size of the nipple is maintained when the mold is removed from the breast.

In another variation, a breast enlargement apparatus may be utilized where the apparatus generally comprises a cup or mold which is sized for placement over a preexisting breast. The cup or mold may define a vacuum port which is sealable and an inner surface of the cup or mold may comprise an adhesive for securement to breast tissue.

BRIEF DESCRIPTION OF THE DRAWINGS

FIGS. 1A to 1D show partial cross-sectional side views of a nipple forming mold adhered to a post-mastectomy breast.

DETAILED DESCRIPTION OF THE INVENTION

Figures 2A, 2B, 2C:
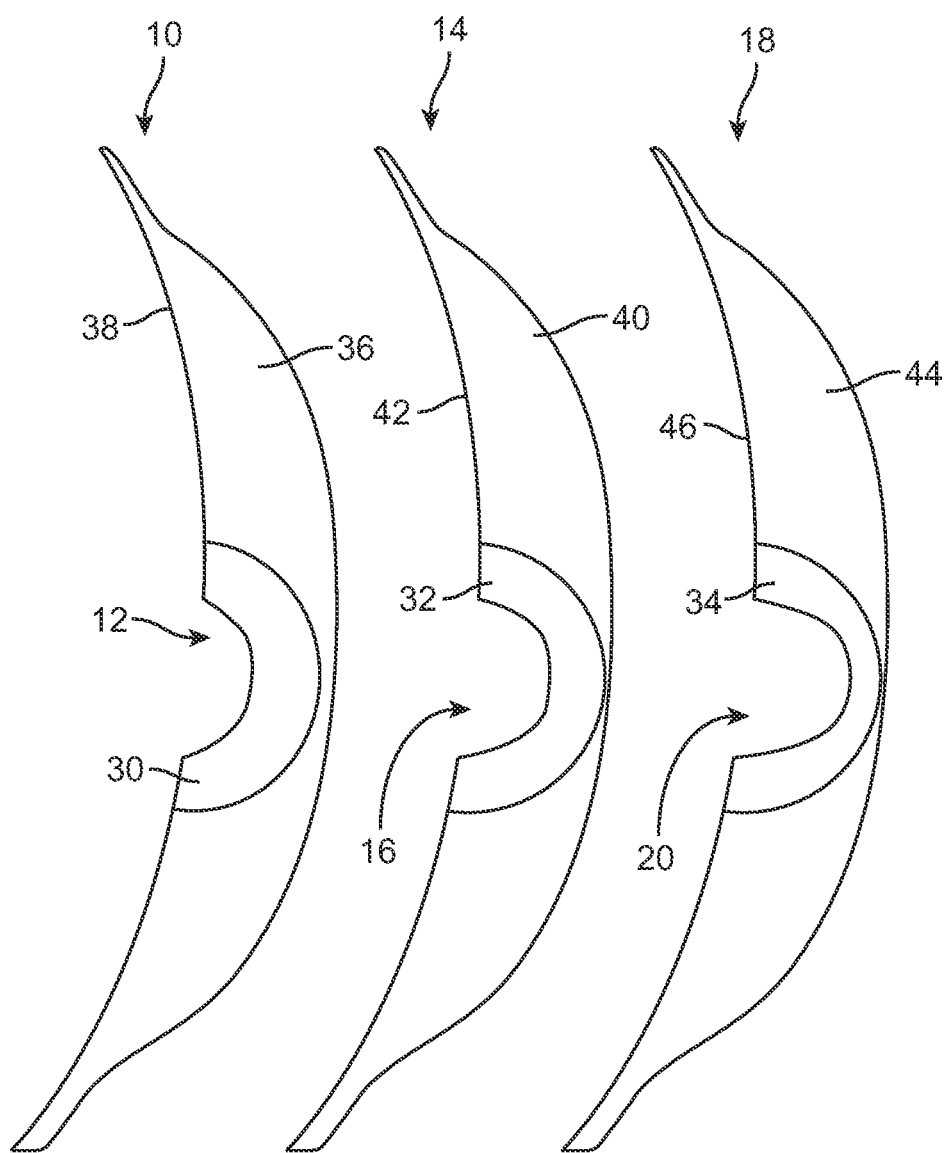
FIGS. 2A to 2C show partial cross-sectional side views of another example of molds which may be used subsequently.

Generally, the cause of nipple flattening is multi-factorial and includes inadequate subcutaneous fat, internal pressure, external pressure, poor flap design, delayed healing, and tissue memory. Poor flap design, inadequate subcutaneous fat and delayed healing are more related to surgical technique. The devices and methods described herein address the internal and external pressures and tissue memory. This is because many materials that have been used as a nipple implant typically reduces in projection over time, whether a permanent implant like ARTECOLL® (Artes Medical, Inc., San Diego, Calif.) or absorbable allografts like ALLODERM® (LifeCell Corp., Branchburg, N.J.).

Generally, the devices described herein precondition, expand or maintain the target nipple tissue (which is homogenous post-mastectomy) which reduces the pressure exerted on an implant by the skin This can be done multiple ways where one variation may utilize an external mold that is adhered to the nipple target skin to create laxity in the skin prior to the implantation of a filler, whether fat or a biomaterial. Once the nipple skin is expanded, an implant such as ALLODERM® or a cylinder of hyaluronic acid threads or a chitosan sponge, for example, is surgically implanted. By creating a space, the forces acting on the nipple implant to drive it into the body may be minimized or rendered non-existent. In another variation designed to maintain nipple tissue, after implanting a filler to create the nipple shape, an external mold is adhered to the newly created nipple projection to reduce or eliminate the external pressure exerted by the skin on the implant while the skin remodels, allowing the nipple projection to be maintained.

One example is shown in the partial cross-section views of FIGS. 1A to 1D. In this variation, a first nipple forming mold 10 may be adhered to a post-mastectomy breast B which has had its nipple surgically removed. The mold 10 may comprise an elastomeric material which has a formed external shaped which is configured to match the contour of the underlying breast B. The contact surface 38 of the mold 10 which contacts the breast B may have an adhesive layered upon the surface 38 to adhere the mold 10 directly to the skin of the breast B. The mold 10 may also define a pocket 12 into which the nipple N, or soon-to-be nipple skin, is to be adhered directly via an adhesive surface. The nipple skin N may be undersized to the nipple mold 10 if the device is used to expand the nipple tissue. If the device is used to maintain the nipple tissue N, a nipple mold which is equally sized to the nipple may be used.

One or more molds may be utilized in progression where each subsequent mold may define a nipple mold which is progressively larger than the previous mold to subsequently stretch the nipple into a progressively larger size. For example, a first mold 10 having a first pocket or nipple cavity 12 may be used to form a nipple N having a first initial shape, as shown in FIG. 1B. After a period of time, e.g., one to three weeks (for instance, two weeks), a second mold 14 having second nipple cavity 16 larger in size than the first pocket 12 may replace the first mold 10. The second mold 14 may adhere the nipple tissue to further stretch or size the skin to conform to the larger second nipple cavity 16 to form a relatively larger nipple N', as shown in FIG. 1C. After an additional period of time, e.g., one to three additional weeks (for instance, two additional weeks or four weeks after initial mold placement), a third mold 18 having a third nipple cavity 20 which is relatively larger than the second nipple cavity 16 may replace the second mold 14. The third pocket 20 may adhere the nipple tissue to further stretch and remodel into a nipple N" which is sized to the final shape of the formed nipple. This third mold 20 may be adhered to the breast B for an additional period of time, e.g., one to three additional weeks (for instance, two additional weeks or six weeks after initial mold placement), as shown in FIG. 1D. Alternatively, additional molds of incremental sizes may be used for various periods of time depending upon the desired shape of the final formed nipple. Once the progression of one or more molds is completed and the patient has reached their desirable nipple size, expansion may be stopped and an implant material or filler such as fat or a biomaterial may be optionally inserted to permanently form the nipple.

Another example is shown in the cross-sectional side views of FIGS. 2A to 2C which illustrate at least three nipple molds 10, 14, 18 for comparison which may be utilized in sequence over a period of time. FIG. 2A shows a first mold 10 having a first nipple cavity 12 which may be utilized to form an initial nipple size. The mold 10 may be formed of a contoured flexible body 36 which is curved or arcuate and forming a contact surface 38 which is shaped to conform to the size of the underlying breast surrounding the tissue region where the nipple is to be formed. The mold body 36 may have a separate portion 30 which is integrated, attached, or otherwise formed with the mold 36 where the nipple is to be formed. This separate portion 30 may be formed to have a stiffness or durometer which is similar or identical to the mold body 36 or its stiffness or durometer may be relative stiffer than the remaining mold body 36. In either case, the nipple cavity 12 for adhering to the tissue has a first size which forms a small protrusion for the nipple. This initial mold may be utilized on the patient for a period of, e.g., one to three weeks, until a second subsequent mold 14, as shown in FIG. 2B, may be used to replace the first mold 10. The second mold 14 may have a size and shape which is similar to the first mold 10 but its nipple cavity 16 may have a second size which is larger than the first nipple cavity 12. Moreover, the second mold 14 may be formed of a second mold body 40 which forms a contact surface 42 which is curved or arcuate for conforming to the size and shape of the underlying breast B. The second nipple cavity 16 may also be formed of a separate portion 32 relative to the mold body 40 in a similar manner to that of the first mold 10. This second mold 14 may be utilized on the patient for a period of, e.g., one to three additional weeks, until a third subsequent mold 18 may be used.

The third mold 18, which is shown in FIG. 2C, may also have a size which is similar to the first 10 and/or second mold 14 but its nipple cavity 20 may have a third shape which is larger than the second nipple cavity 16. The third nipple cavity 20 may approximate the final size of the desired nipple shape. Moreover, this third mold 18 may be utilized on the patient for at least, e.g., one to three additional weeks, as well. Similarly to the other molds, the third mold 18 may also be formed of a flexible mold body 44 which is curved or arcuate for conforming to the breast and nipple with an optional portion 34 integrated or otherwise attached to the remaining mold body 44. While the molds are shown for use and replacement during, e.g., week 2, week 4, and week 6 of the procedure, fewer or greater number of molds may be used to vary the degree to nipple enlargement and the time periods during use of each mold may also be varied as well depending upon the desired results and comfort of the patient.

Figure 3A:
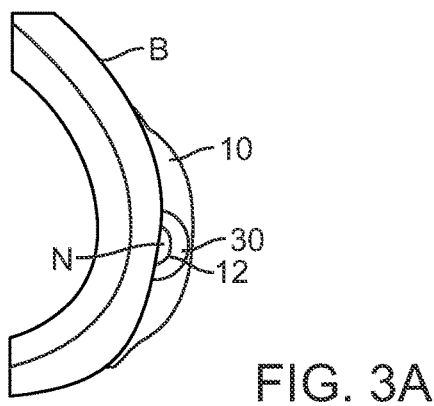
FIGS. 3A and 3B show partial cross-sectional side views of another example of application of a first mold having a first nipple cavity.
Figure 3B:
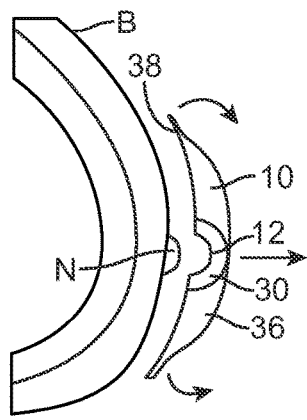
Figure 4A:
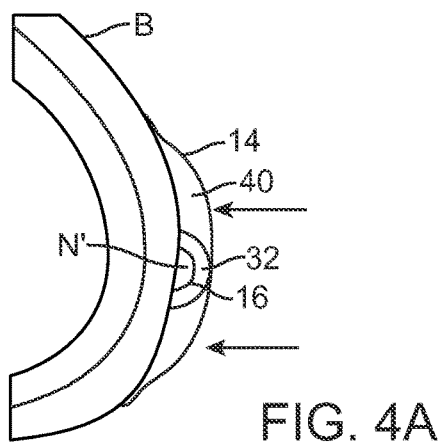
FIGS. 4A and 4B show partial cross-sectional side views of another example of application of a second mold having a second nipple cavity sized larger than the first nipple cavity.
Figure 4B:
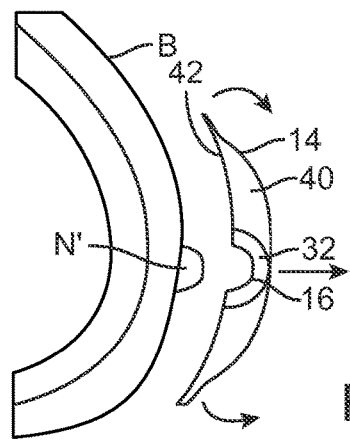
Figure 5A:
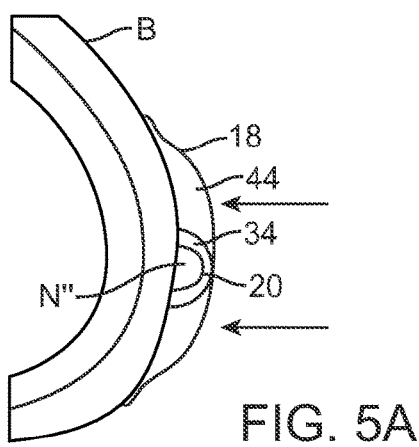
FIGS. 5A and 5B show partial cross-sectional side views of another example of application of a third mold having a third nipple cavity sized larger than the second nipple cavity.
Figure 5B:
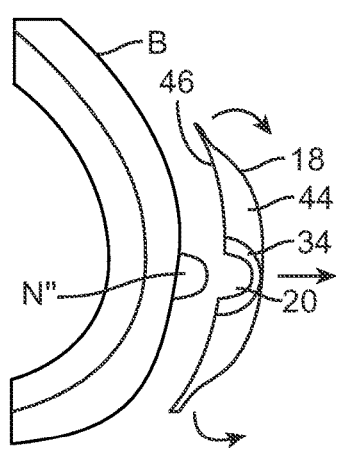

FIGS. 3A and 3B show cross-sectional side views which illustrate one example of use for the first nipple mold 10 where after the patient has worn the initial mold 10 for a predetermined period of time, the contact surface 38 of the first mold 10 may be peeled away from the breast B and nipple N and replaced by the second mold 14, as shown by FIGS. 4A and 4B. Once the nipple N' has enlarged to the larger second nipple cavity 16, the contact surface 42 of the second mold 14 may be removed and the third mold 18 may be adhered to the breast B, as shown in FIGS. 5A and 5B. Once the nipple N" has again enlarged to the size of the third nipple cavity 20 which is larger than the second nipple cavity 16, the mold 20 may be removed. If the nipple N" has increased in size to the desired degree of protuberance, the treatment may be completed; otherwise, yet another mold having a larger nipple cavity may be adhered to the breast B and the treatment continued until the desired degree of skin laxity and resulting nipple shape has been achieved.

Placement of the first mold 10, second mold 14, and/or third mold 18 (and any number of subsequent molds) may be accomplished by inverting the mold from its initial shape, as shown in FIG. 3A, to an inverted shape where the contact surfaces along the mold and in the nipple cavity are exposed or presented for placement against the skin (Examples of mold inversion are described in further detail below.)

Once the mold has been inverted, the contact surface may be placed or positioned upon the skin surface and the mold may then be allowed to re-invert back to its relaxed configuration. As the mold 10 re-inverts, the underlying skin may be pulled or recruited into the nipple cavity 12 (e.g., by adhesive, vacuum, etc.) and maintained in position as the remainder of the mold 10 comes into contact against the remainder of the breast tissue. Removal of the mold 10 may be accomplished by inverting the mold 10 again and pulling from the skin surface. The process, as described above, may be repeated with each subsequent mold while increasing the size of formed nipple N.

Figure 6A:
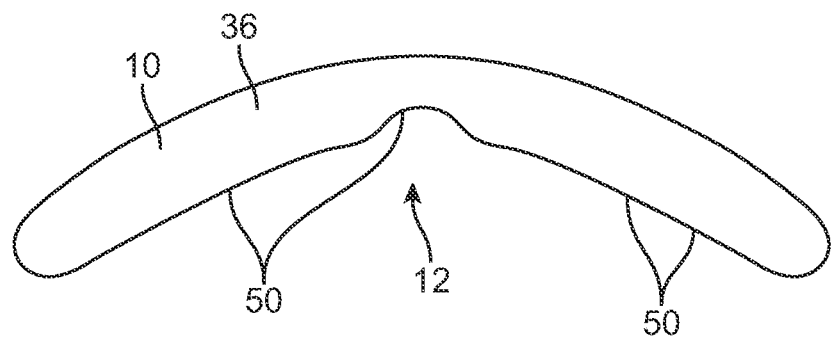
FIGS. 6A and 6B show side views of another variation of a mold which is invertible.
Figure 6B:
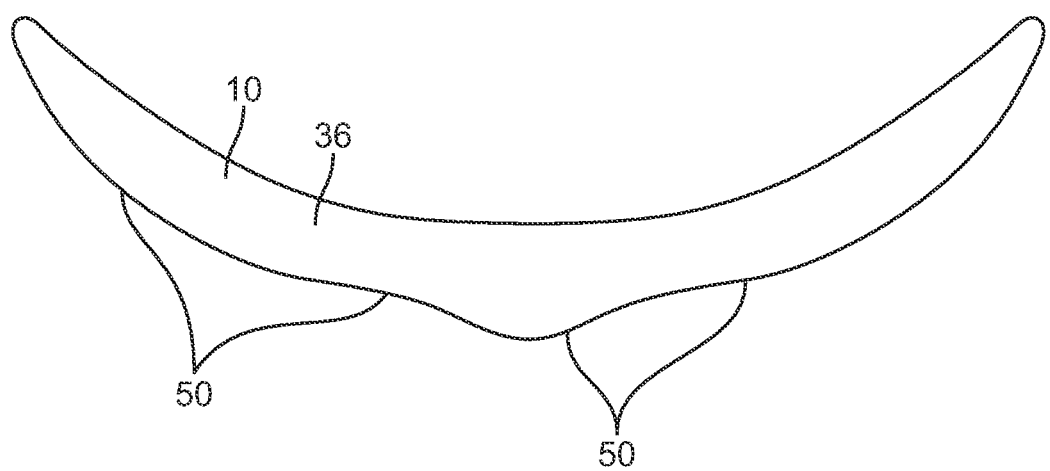
Figure 6C:
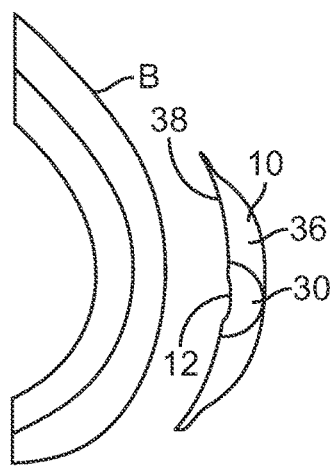
FIGS. 6C to 6G illustrate an example of how an invertible mold may be applied to a breast and subsequently removed.
Figure 6D:
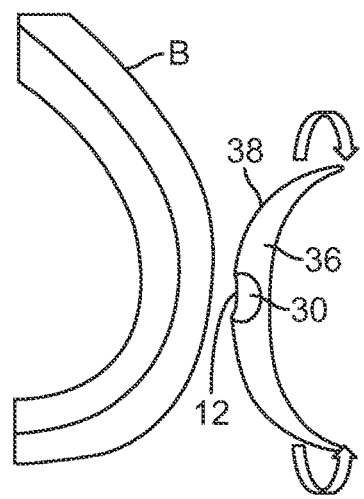

An example of nipple mold 10 is shown in the side view of FIG. 6A, which illustrates a device which may be inverted to allow for easy adherence of the nipple skin to the mold device, as shown in FIG. 6B. In this example, mold 10 may optionally have a biocompatible adhesive layer 50 to attach the mold 10 to the skin of the breast B as well as the skin for forming the nipple. The adhesive layer 50 may be formed of any number of temporary biocompatible adhesives. FIGS. 6C to 6G illustrate cross-sectional side views of one example of how an invertible mold may be applied to a breast B and then subsequently removed once the nipple has been desirably formed. As shown in FIG. 6C, the contact surface 38 of mold 10 may be brought into proximity to the breast B in the area where the nipple is to be formed. The mold 10 may then be inverted to expose the nipple cavity 12 for direct adherence onto the tissue region, as shown in FIG. 6D. With the mold inverted, the mold 10 may be adhered onto the breast tissue surface either via a negative pressure created by the mold 10 being pressed directly against the skin when inverted and re-inverted, the adhesive layer 50 on the contact surface 38, and/or optionally through a vacuum force (or any combination thereof) which may be formed by placing the mold 10 onto the skin By inverting the mold 10, the underlying skin may be well adhered especially as the mold 10 is reverted into its original shape for placement upon the remainder of the breast.

Figure 6E:
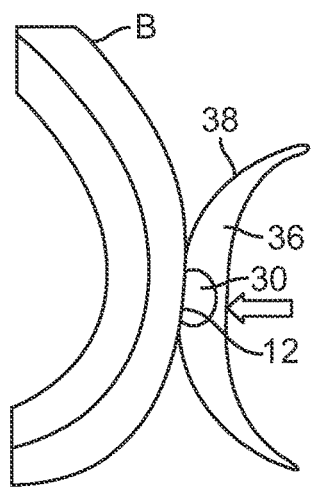
Figure 6F:
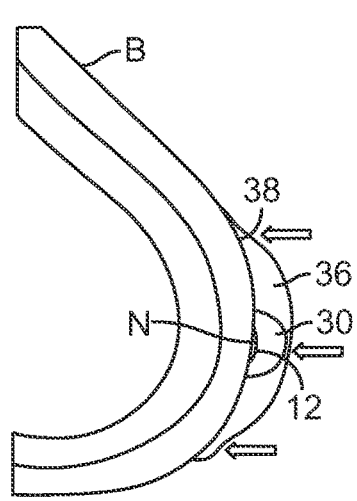
Figure 6G:
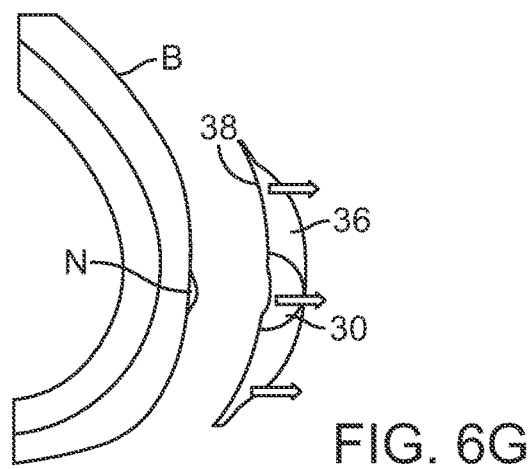

As the mold 10 reverts, it may pull or recruit the skin into the nipple cavity 12, as shown in FIG. 6E, and the remainder of the contact surface of the mold 10 may be pressed against the surrounding skin of the breast B, as shown in FIG. 6F, and the mold 10 may be maintained in its position for a predetermined period of time until the tissue within the nipple cavity 12 has achieved sufficient laxity to form the nipple N. Once the nipple N has been desirably formed, the mold 10 may be removed, as shown in FIG. 6G, by simply pulling the mold 10 from the skin and nipple N or re-inverting the mold 10 back into its inverted shape to facilitate its release from the skin and a subsequent mold having a larger nipple cavity may be optionally applied in the same manner to further protrude the nipple, if necessary or desired.

Figure 7:
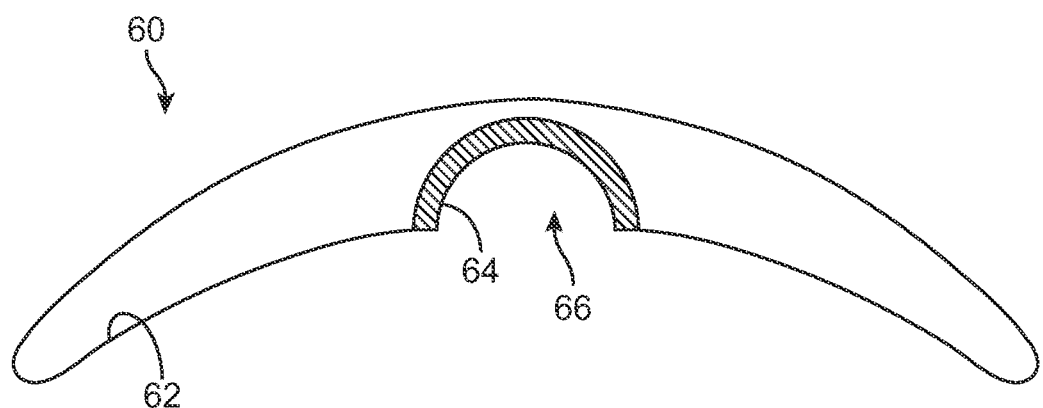
FIG. 7 shows a side view of another variation of a mold having at least two regions of differing stiffness.

Another variation 60 is shown in the partial cross-sectional side view of FIG. 7 which illustrates a dual durometer design where the molding pocket 66 for the nipple may be formed of a material 64 having a higher stiffness or durometer relative to the remainder of the mold body 62 which may have a relatively lower stiffness or durometer. The dual durometer design may allow for restriction of the nipple while still allowing for a relatively freer or more natural movement of the device as well as the remainder of the breast.

Figure 8:
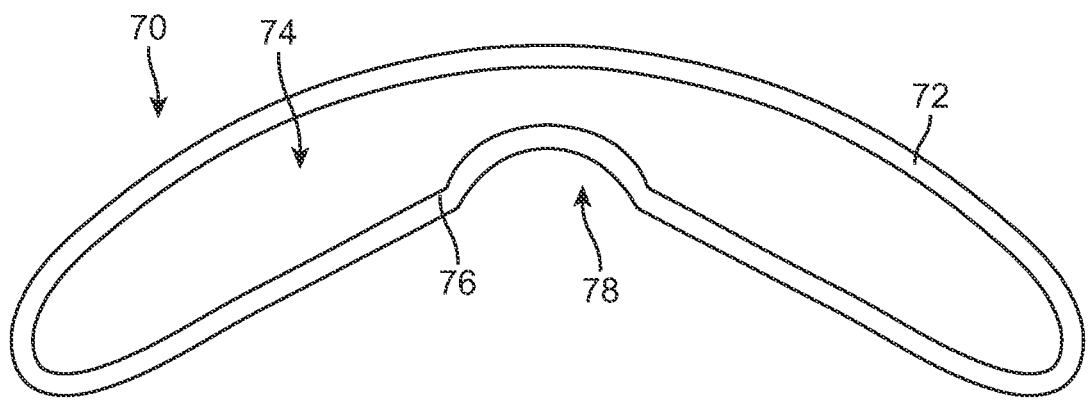
FIG. 8 shows a partial cross-sectional side view of another variation of a mold which is hollowed.

Yet another variation 70 is shown in the partial cross-sectional side view of FIG. 8 which shows a molding device formed from a molding shell 72 having an interior portion 74 which is hollow to minimize the mass and weight of the device. Optionally, the material 76 forming the nipple pocket 78 may have a thickness which is greater than the thickness of the remainder of the mold such that the resulting stiffness of the nipple pocket 78 is relative higher than the remainder of the device to allow for a relatively freer and more natural movement of the breast while still restricting the nipple adhered within the pocket 78.

Figure 9A:
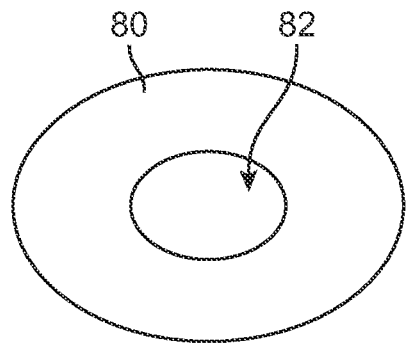
FIGS. 9A to 9E illustrate an example of a nipple mold device which is distensible into an enlarged condition for placement upon the breast to cinch or bunch the breast tissue into a nipple.
Figure 9B:
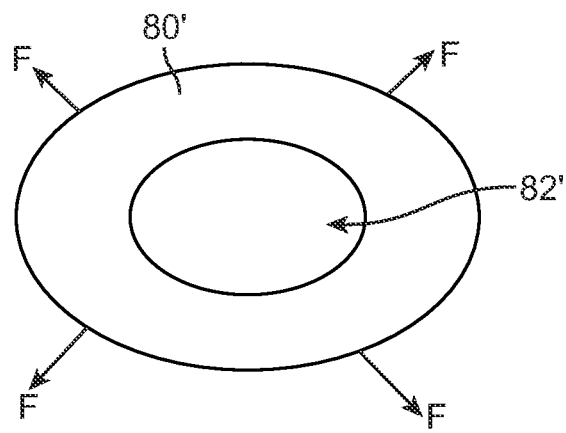
Figure 9C:
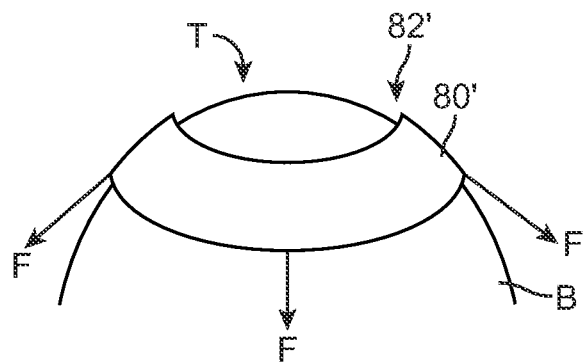
Figure 9D:
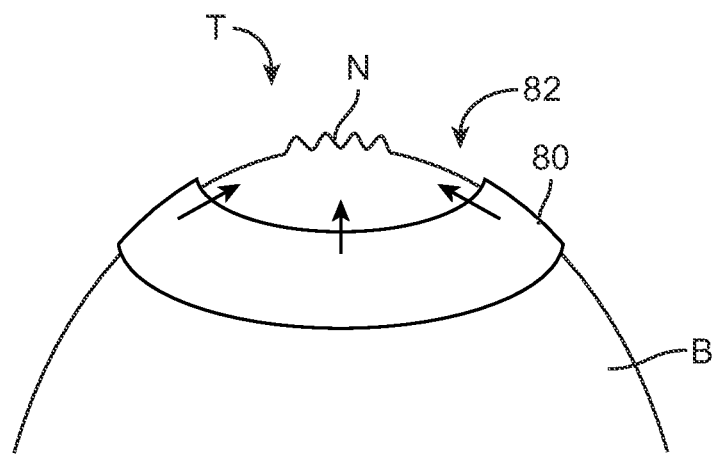
Figure 9E:
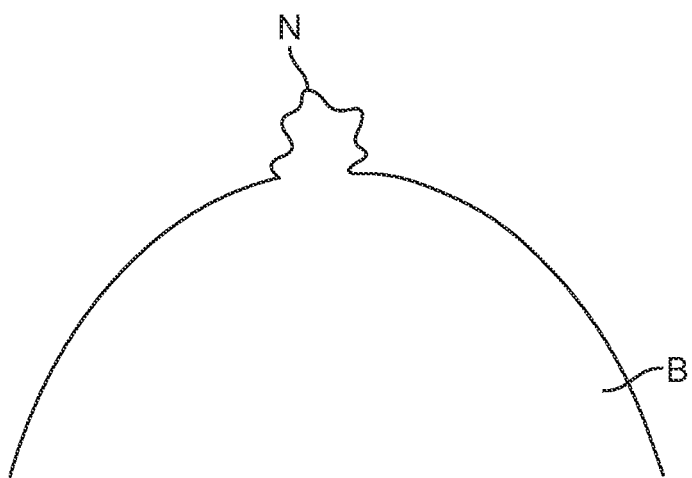

In another variation, the nipple molding device or a separate radially compressive mold 80 may be designed to be radially compress the skin surrounding the nipple to generate the appropriate skin laxity. This may be accomplished alone or in combination with a forming mold or a template, as described above. As shown in the variation of FIGS. 9A to 9E, the nipple mold device 80 may be formed of, e.g., an elastomeric ring defining an open area 82 within where the nipple tissue is to be formed. The device 80 may have a relaxed and un-stretched shape as shown in the bottom view of FIG. 9A. Prior to adhering the device to the breast, the mold 80 may be stretched radially 80' by a preset or predetermined amount by a force F, as shown in FIG. 9B, such that the mold and the open area 82' is stretched radially. With the nipple mold stretched into its expanded shape 80', the device may be adhered upon the breast B such that the tissue region T of the nipple (or to-be-formed nipple) is encircled by the device, as shown in FIG. 9C. Once adhered to the skin of the breast, the device 80 may be free to retract back towards its natural state, as shown in FIG. 9D, such that the device cinches or bunches the tissue T to be formed into the nipple N. Once the mold 80 has been adhered onto the breast for the desired period of time, or once the one or more succession of molds have been utilized to subsequently increase the shape of the nipple to the desired size, the resulting nipple N may be formed upon the breast B, as shown in FIG. 9E.

Figure 10:
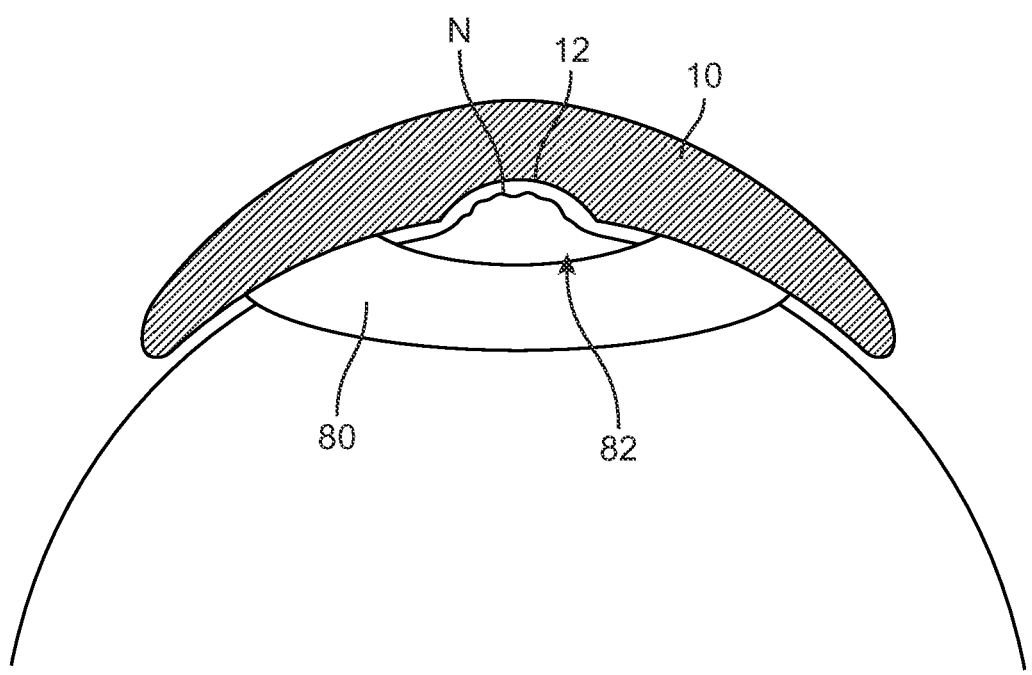
FIG. 10 illustrates a partial cross-sectional side view of another example where a mold may be utilized in combination with a distensible nipple molding device.

FIG. 10 shows an example of another variation where the radially compressive molding device 80 may be utilized in combination with any of the nipple molding devices 10 described herein. In this example, the radially compressive mold 80 and the nipple mold 10 may be utilized either simultaneously or sequentially.

Figure 11A:
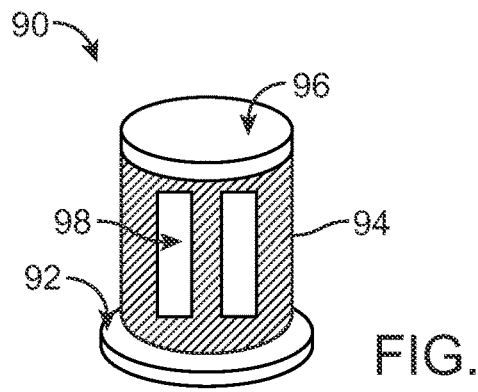
FIGS. 11A to 11D show perspective and partial cross-sectional side views of another variation of a nipple forming device having an adjustable column.
Figure 11B:
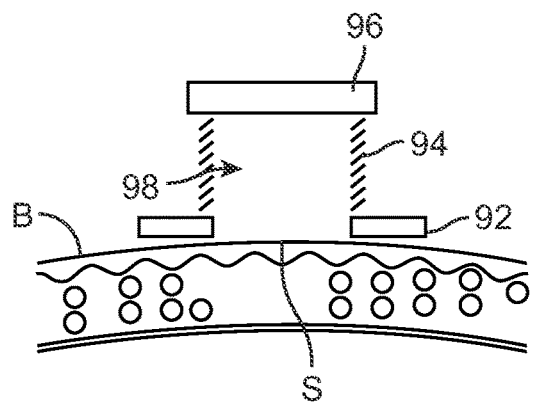

In yet another example, FIG. 11A shows a perspective view of a nipple forming device 90 which may be adjusted in height to optionally control the size or degree to which the formed nipple projects from the breast. The device 90 may generally comprise a base 92 (e.g., having a base of 3 cm) which may be adhered to the surface of the breast B and a column 94 which may be threaded to optionally adjust a height (e.g., anywhere between 0.5 to 2.5 cm or more) of a biasing mechanism 96 (e.g., a magnet) relative to the base, as shown in FIG. 11B. The column and base may define an opening or cavity 98 into which the nipple may project for formation.

Figure 11C:
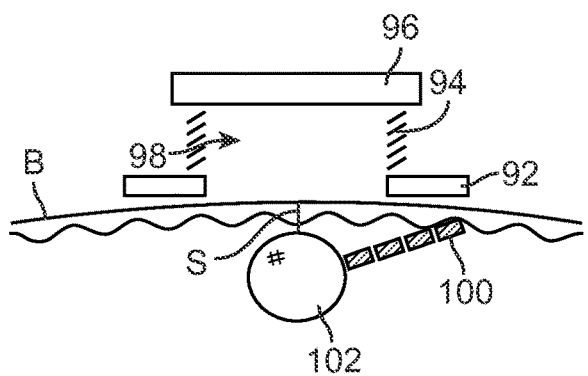
Figure 11D:
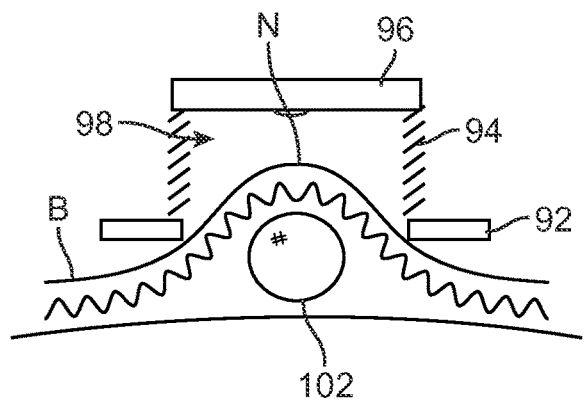

With the device 90 positioned over the region of the breast where the nipple is to be formed such as over a scar S where the original nipple has been removed, an implant 102 (e.g., a magnet coated with silicone) having a diameter of, e.g., 6 to 8 mm, may be inserted into the breast tissue through an incision 100 adjacent to the device 90 and beneath the base of the device, as shown in FIG. 11C. In the event that biasing mechanism 96 comprises a magnet, the implant 102 may simply comprise a coated ferromagnetic material (such as ferromagnetic stainless steel having low magnetic remanance). With this variation, the magnet in biasing mechanism 96 may attract the implant 102. Over time, the implant 102 may be drawn outward from the breast tissue and into the opening or cavity 98 by the attraction between the magnet in the implant 102 and the magnet in the biasing mechanism 96, as shown in FIG. 11D, to stretch the skin and to form the nipple N projecting from the breast. Once the nipple N has been desirably stretched and remodeled, the base 92 and biasing mechanism 96 may be removed from the breast B and the ferromagnetic implant 102 may be left in the breast B.

Figure 11E:
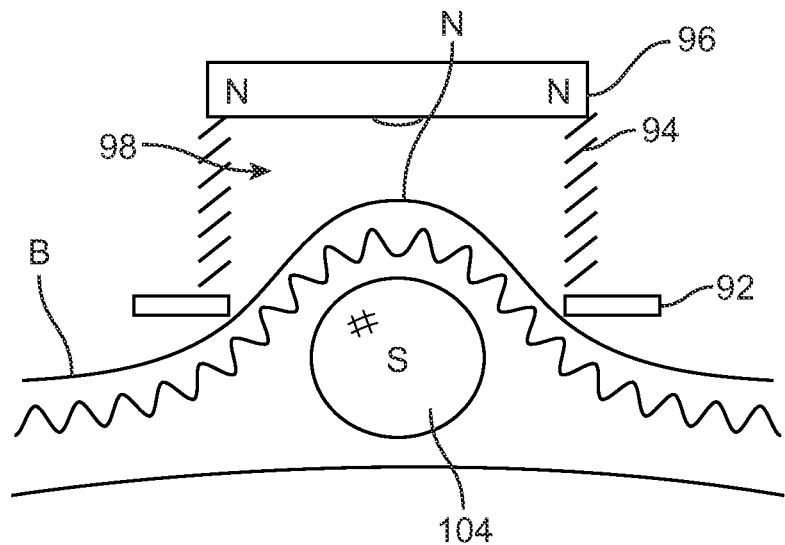
FIG. 11E shows a partial cross-sectional side view of another variation where both the biasing mechanism and nipple implant comprise magnets of opposite polarity to provide the attractive force between to stretch and remodel the nipple tissue.
Figure 11F:
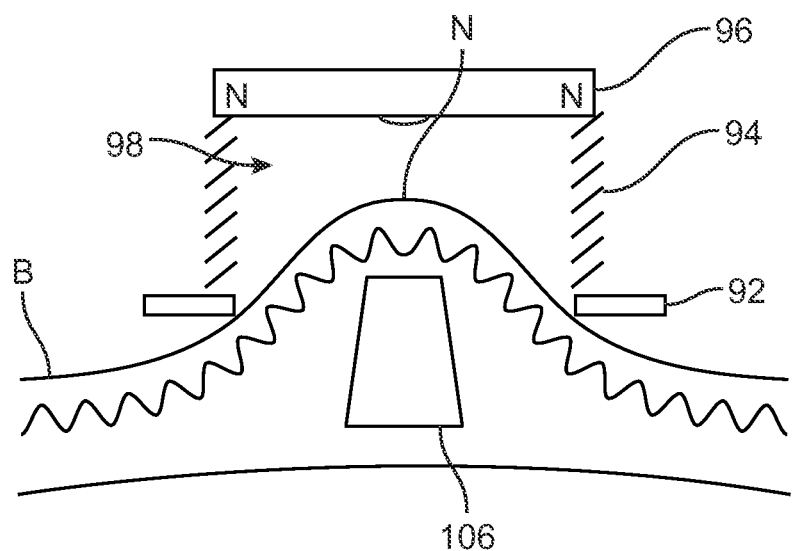
FIG. 11F shows a partial cross-sectional side view of yet another variation where a magnetic nipple implant may be removed and subsequently replaced with a filler or non-magnetic implant.

FIG. 11E illustrates an example where the implanted portion comprises a magnet 104 having an opposite polarity from that of biasing mechanism 96, which is shown as a complementary magnet for providing the attractive force between each respective magnet 96, 104. Once the nipple N has been sufficiently stretched and remodeled, the base 92 and magnet 96 assembly may be removed from the breast B and the remaining magnet 104 may be left in place. Alternatively, rather than leaving magnet 104 in the breast, a second procedure may be performed to remove magnet 104 through an incision and replace it with a filler material or polymeric nipple implant 106 (e.g., non-magnetic or non-ferrous) as described herein and as shown in FIG. 11F.

Figure 12A:
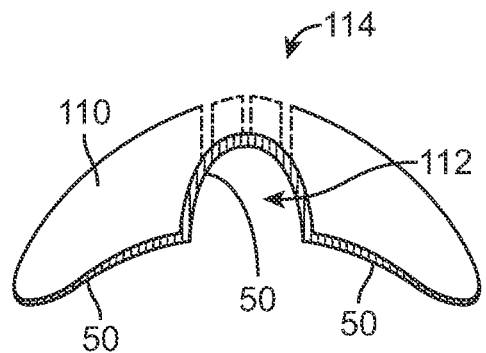
FIGS. 12A to 12D show partial cross-sectional side views of yet another variation of a mold which defines one or more ports through which a vacuum may be drawn to ensure adherence of the tissue within the nipple cavity.

In yet another variation, another embodiment may comprise stretching the breast tissue to form the nipple with the assistance of a suction or vacuum force. As shown in the partial cross-sectional side view of FIG. 12A, the molding device may comprise a contoured mold 110, as previously described, but also including one or more openings 114 through the device in communication with the nipple molding cavity 112.

Figure 12B:
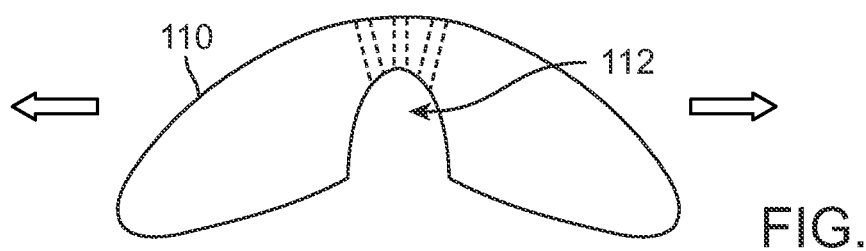
Figure 12C:
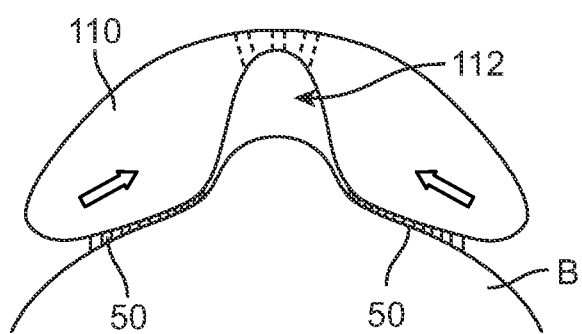
Figure 12D:
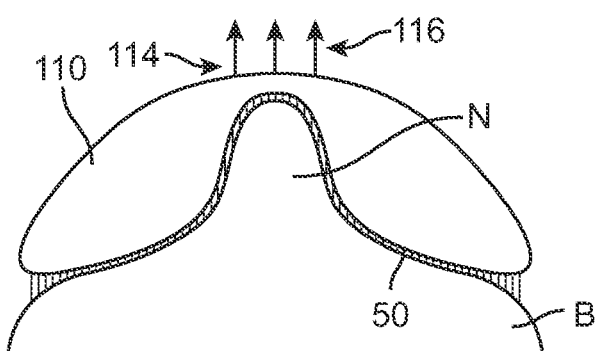

In use, the device 110 may be optionally stretched in a radial direction, as shown in FIG. 12B, and then adhered upon the breast in the area where the nipple is to be formed. When the device 110 is released and allowed to retract back towards its relaxed configuration, the adhered breast tissue B may be pulled to create skin laxity within the nipple molding cavity 112, as shown in FIG. 12C. A vacuum or suction force 116 may be optionally applied through the openings 114 via a vacuum pump to further draw the skin into the nipple molding cavity 112 to ensure adherence of the skin to the mold, as shown in FIG. 12D. Once the tissue has been adhered and the nipple N formed within the cavity 112, the vacuum may be removed.

Figure 13A:
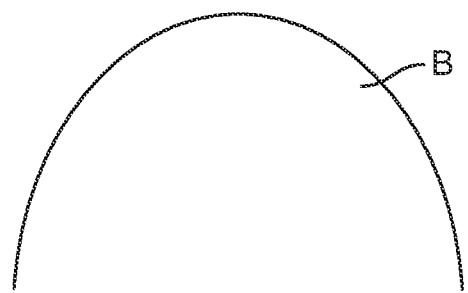
FIGS. 13A to 13C illustrate an example for forming a nipple where an implant may be inserted within the breast prior to the application of a mold.
Figure 13B:
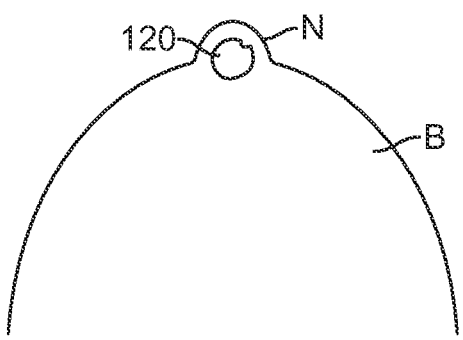
Figure 13C:
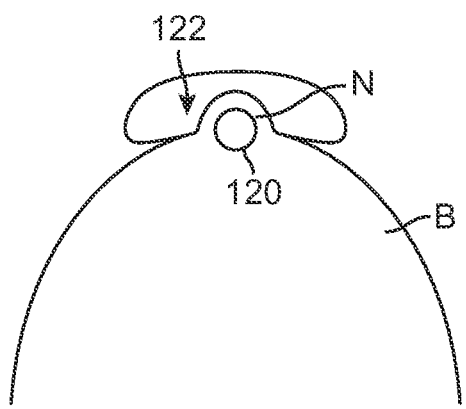

In yet another variation, a nipple implant filler 120 may be inserted into the breast tissue B where the nipple is to be formed, as shown in FIGS. 13A and 13B. A nipple forming mold 122 may then be positioned over the implant 120 to hold the nipple shape long enough for the skin to remodel, as shown in FIG. 13C. In this variation, the forming mold may be utilized to maintain the shape of the nipple which is already formed by the implant and further prevent the extrusion of the implant into the body. Accordingly, a forming mold 122 which has a nipple forming cavity corresponding to the final desired nipple shape or which has a cavity which is larger than the desired shape may be utilized for a predetermined period of time until the skin forming the nipple has incurred sufficient laxity. The implant may generally comprise any number of biocompatible filler material or any number of conventional implants such as ARTE-COLL® or absorbable allografts like ALLODERM®, as mentioned above.

Figure 14A:
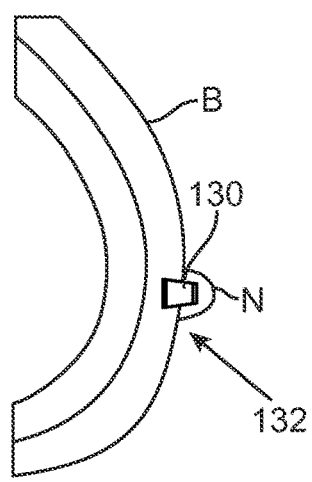
FIGS. 14A to 14E illustrate another example of subsequent molds utilized after the implantation of a nipple implant.
Figure 14B:
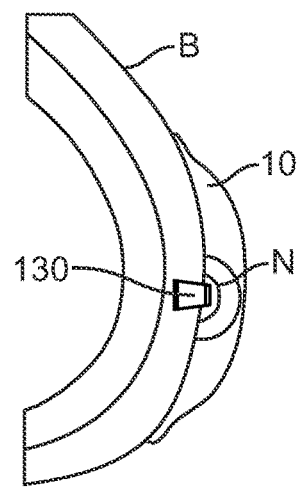
Figure 14C:
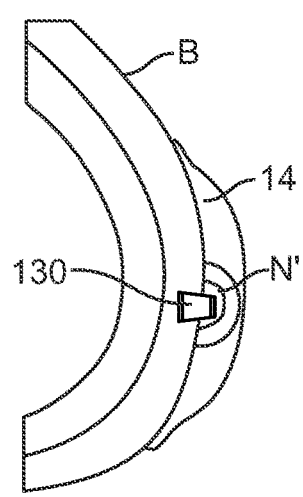
Figure 14D:
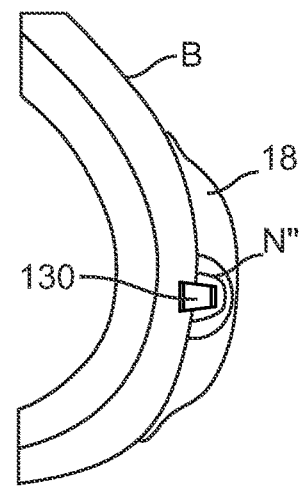
Figure 14E:
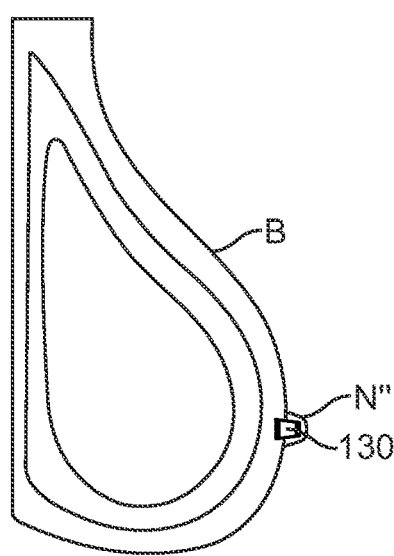

Cross-sectional side views of yet another illustration of utilization of multiple molds are shown in FIGS. 14A to 14E. In this example, once an implant 130 (e.g., any of the filler materials described herein) has already been inserted into the breast B to form an initial nipple N, a first mold 10 having a first nipple cavity may be adhered to the breast B and to the nipple N directly and the mold 10 may be maintained in position for the predetermined period of time, as described above and as shown in FIG. 14B. Subsequently, the first mold 10 may be removed and a second mold 14 having a second larger nipple cavity may be applied to the breast B and maintained in position for the predetermined period of time, as shown in FIG. 14C. As the larger nipple cavity is applied and the nipple N' protrudes farther out from the breast surface, the implant 130 may also project farther out with the formed nipple tissue, as shown. Additionally, the third mold 18 may then be applied to the breast B with the third nipple cavity which is larger than the second cavity and maintained in position until the nipple N" has enlarged to the desired size and shape, as shown in FIG. 14D. Treatment may be continued if desired or necessary; otherwise, if the treatment is completed, the mold may be removed resulting in the breast with the projected nipple N" having the desired shape and size, as shown in FIG. 14E.

Figure 15C:
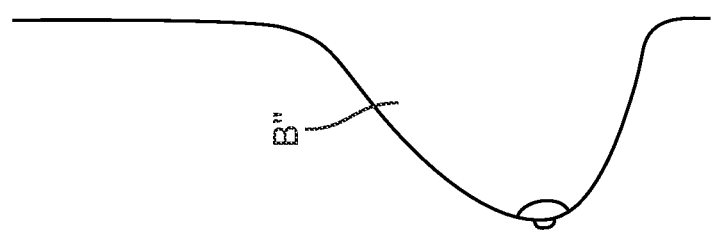
FIGS. 15A to 15C illustrate an example of a breast reconstruction or enlargement device which may be positioned over a breast which is then enlarged into contact against the inner surface of the device and adhered to the inner surface.
Figure 15B:
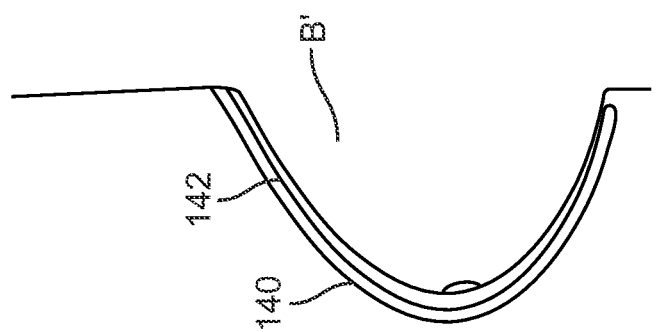
Figure 15A:
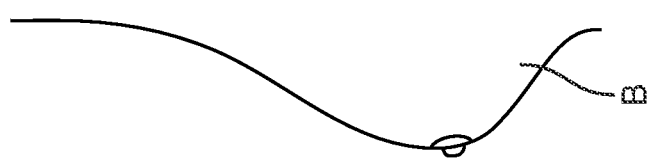

Turning now to devices and methods which may be utilized for breast reconstruction and/or enlargement, FIGS. 15A to 15C show side views of one variation where a cup or mold 140 that is slightly larger than the existing breast size may be adhered over the breasts B. The oversized cups 140 may have an inner surface 142 to which the skin of the breast B may be adhered to such that the forces imparted on the breast B', B" to impart expansion by creating the skin laxity are continuous but would not require a pump. Furthermore, they could be worn continuously which may generate results faster than conventional pump mechanisms.

Figure 16D:
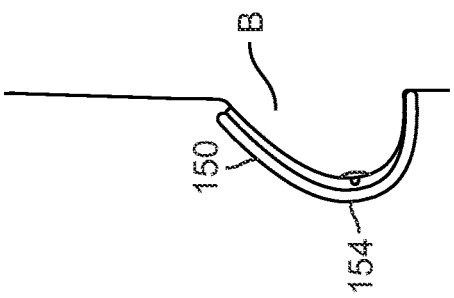
FIGS. 16A to 16D show perspective and partial cross-sectional side views of another variation of the breast reconstruction or enlargement device which defines one or more openings for communication with a vacuum.
Figure 16C:
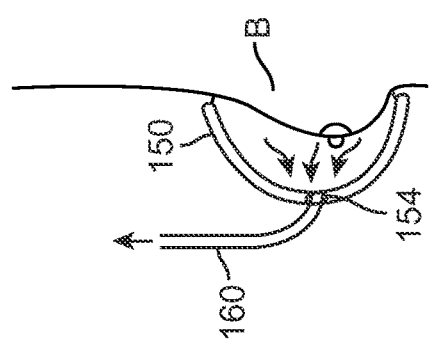
Figure 16B:
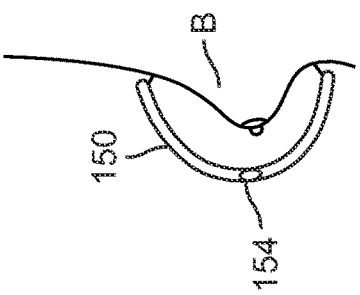
Figure 16A:
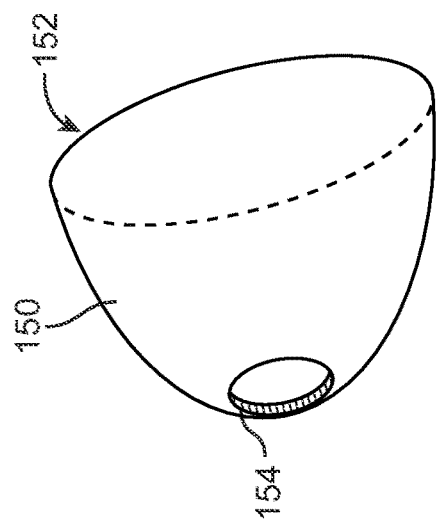

Another variation is shown in the perspective view of FIG. 16A which illustrates a cup or mold 150 having an opening 152 through which the breast or breasts are placed and which defines an opening or port 154 through which the nipple may be positioned and/or through which a vacuum force may be suctioned via a tubing 160 optionally detachable through opening or port 154 to ensure the initial contact between the mold 150 and the breast tissue. As illustrated in FIG. 16B, the cup or mold 150 may be placed over the breast B and a vacuum force may then be drawn to initially enlarge the breast B into contact against the inner surface of the cup or mold 150. Once the breast B has been enlarged and securely adhered to the cup or mold 150, the vacuum may be removed. Because the breast B is adhered to the inner surface of the cup or mold 150, there is no need for sealing for continued application of any vacuum force, as shown in FIG. 16D.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A nipple forming assembly, comprising:
    a first mold having a first contact surface which is curved in conformance with a breast upon which the first mold is positionable, wherein the first contact surface comprises an adhesive for securement upon the breast;
    at least a second mold having a second contact surface which is curved in conformance with the breast upon which the second mold is positionable, wherein the second contact surface comprises an adhesive for securement upon the breast; and,
    an implant approximating a size of a nipple to be formed upon the breast,
    wherein the first mold defines a first cavity along the first contact surface which defines a relatively reduced size of the nipple to he formed upon the breast such that the first cavity at least partially encompasses the implant and where the first cavity further comprises the adhesive for securement to the nipple to he formed, wherein the first mold has a first thickness yielding a first stiffness and the first cavity of the first mold has a second thickness yielding a. second stiffness which is higher than the first stiffness such that the nipple is restricted; and
    wherein the second mold is sized for use upon the breast after a predetermined period of time in a sequence following application of the first mold upon the breast and where the second mold defines a second cavity along the second contact surface which is relatively larger than the first cavity such that the second cavity at least partially encompasses the implant and where the second cavity further comprises the adhesive for securement to the nipple to be formed such that the nipple and the implant are forced to protrude relatively farther out from a surface of the breast when adhered to the second cavity than when adhered to the first cavity.

2. The assembly of claim 1 wherein the first mold is invertible.

3. The assembly of claim 1 further comprising:
    at least a third mold having a third contact surface which is curved in conformance with the breast upon which the third mold is positionable, wherein the third contact surface comprises an adhesive for securement upon the breast,
    wherein the third mold defines a third cavity along the third contact surface which is relatively larger than the second cavity such that the third cavity at least partially encompasses the implant and where the third cavity further comprises the adhesive for securement to the nipple to be formed.

4. The assembly of claim 1 wherein the implant comprises a biocompatible filler material.

* * * * *